US008162954B2

(12) United States Patent
George et al.

(10) Patent No.: US 8,162,954 B2
(45) Date of Patent: Apr. 24, 2012

(54) UTERINE MANIPULATORS

(76) Inventors: Samuel George, Weybridge (GB);
Abdul Raheem Haloob, Brentwood (GB)

(*) Notice: Subject to any disclaimer, the term of this patent is extended or adjusted under 35 U.S.C. 154(b) by 265 days.

(21) Appl. No.: 12/297,749

(22) PCT Filed: Apr. 17, 2007

(86) PCT No.: PCT/GB2007/001401
§ 371 (c)(1),
(2), (4) Date: Jan. 19, 2009

(87) PCT Pub. No.: WO2007/129013
PCT Pub. Date: Nov. 15, 2007

(65) Prior Publication Data
US 2009/0137970 A1 May 28, 2009

(30) Foreign Application Priority Data
Apr. 21, 2006 (GB) .................................. 0607885.1

(51) Int. Cl.
*A61B 17/42* (2006.01)
(52) U.S. Cl. ...................................................... 606/119
(58) Field of Classification Search ................. 600/591; 604/103.03, 279; 606/119, 121–126, 193
See application file for complete search history.

(56) References Cited

U.S. PATENT DOCUMENTS

| 3,796,211 | A | | 3/1974 | Kohl | |
|---|---|---|---|---|---|
| 4,016,867 | A | * | 4/1977 | King et al. | 600/591 |
| 4,089,337 | A | | 5/1978 | Kronner | |
| 4,489,732 | A | * | 12/1984 | Hasson | 600/591 |
| 4,997,419 | A | * | 3/1991 | Lakatos et al. | 604/523 |
| 5,147,316 | A | * | 9/1992 | Castillenti | 604/164.04 |
| 5,368,598 | A | | 11/1994 | Hasson | |
| 6,423,075 | B1 | | 7/2002 | Singh et al. | |
| 6,706,026 | B1 | | 3/2004 | Goldstein et al. | |
| 2005/0085827 | A1 | * | 4/2005 | G. et al. | 606/119 |

FOREIGN PATENT DOCUMENTS

| DE | 20 2004019868 | 3/2005 |
|---|---|---|
| WO | WO9600105 | 1/1996 |
| WO | WO9738637 | 10/1997 |
| WO | WO2006120451 | 11/2006 |

OTHER PUBLICATIONS

International Search Report of PCT/GB2007/001401 dated Feb. 25, 2008.

* cited by examiner

*Primary Examiner* — Ryan Severson
(74) *Attorney, Agent, or Firm* — Caesar, Rivise, Bernstein, Cohen & Pokotilow, Ltd.

(57) ABSTRACT

Universal laparoscopic uterine manipulators/dilators with variable intra-uterine length to match the length of the uterus in order to avoid any risk of perforation and to provide excellent pelvic exposure irrespective of uterine size, shape and position. Moreover, semirigid/semi-flexible dilators are less likely to form false passages in the cervix and the body of the uterus as they follow the natural track of the cervical canal.

28 Claims, 9 Drawing Sheets

UTERINE MANIPULATORS

The present invention relates to uterine manipulators for use in gynaecological procedures. The invention relates particularly, but not exclusively, to a uterine cannula that may be used for uterine manipulation during laparoscopic procedures. The invention also relates to uterine dilators that may be used for uterine manipulation.

In this specification, the term 'uterine manipulator' encompasses uterine cannulae and uterine dilators that are suitable for uterine manipulation, whether or not they are in fact used for manipulation.

It is common for women to have the patency of their fallopian tubes, or oviducts, assessed as part of investigations into infertility. That assessment involves a hydrotubation procedure in which a dye such as methylene blue is injected into the patient's uterus through the cervix. The passage of dye through the uterus and oviducts may then be tracked using a laparoscope inserted through an abdominal incision to visualise the pelvic region while hydrotubation is carried out. If an oviduct is blocked, the point of blockage can be identified as the point beyond which the dye does not flow. A catheter wire may be used subsequently to unblock the oviduct.

Hydrotubation is performed using a uterine cannula whose shaft is inserted into the vagina and then through the cervix so that a distal end portion of the shaft—an intra-uterine tip—extends into the uterus. The shaft is hollow, defining a conduit for carrying dye or other fluid from a proximal end opening to one or more distal openings in the distal end portion of the shaft. A cervical stop disposed on the shaft at the proximal end of the distal end portion extends radially from the shaft to seal against and within the external os of the cervix, hence retaining the injected fluid within the uterus.

Typically, a tenaculum or volsellum forceps is used to grasp and pull the cervix to stabilize and align the uterine cavity. The forceps may be fixed proximally to the shaft of the cannula, whereby tension applied to the cervix through the forceps equates to pressure applied distally to the shaft to keep the stop in sealing engagement with the cervix.

Once inserted as described above, a uterine cannula may also be used to manipulate the uterus to ease laparoscopic visualisation of the uterus, the oviducts and other associated structures in the pelvic region, notably the ovaries. Movement of the cannula to manipulate the uterus may require the assistance of a second physician while the first physician views the pelvic region through the laparoscope. This increases the cost of the procedure and relies upon effective teamwork and communication between the physicians.

The distal end portion of the shaft of a uterine cannula is preferably narrow to ease insertion into the cervix. There is a risk that the distal end of the shaft may perforate the uterus upon insertion of the cannula or during subsequent manipulation using the cannula. The alternatives of a wider shaft or an enlarged distal end reduce the risk of perforation but increase the risk of cervical tearing and incompetence. As different uteri have various dimensions, particular care must be taken to ensure that the distal end portion of the cannula cannot extend beyond the distal extremity of the uterus, the fundus. It is therefore necessary to measure uterine depth before a uterine cannula is used.

Measurement of uterine depth is typically performed by a sounding procedure using a uterine sound. The uterine sound is inserted through the cervix into the uterus to measure the distance between the cervical os and the uterine fundus. The sound is inserted until resistance is felt when its distal end encounters the fundus. Like a dipstick, the level of wetness or mucus applied by the cervix to the sound indicates the depth of insertion into the uterus. That level may be read off a scale marked on the sound when the sound is withdrawn from the vagina.

A uterine sounding procedure can also help to determine whether the uterus is anteverted (tipped forwards above the cervix, toward the stomach) or, less commonly, retroverted (tipped backwards above the cervix, toward the spine). If the uterus is retroverted, laparoscopic visualisation of the uterus, oviducts and ovaries may be difficult. For this reason, a retroverted uterus must generally be manipulated into an anteverted position before hydrotubation.

The sounding procedure is not always straightforward. Insertion of the sound into the cervix may be difficult if the cervical os is stenosed or awkwardly oriented, and must be performed carefully and gently to avoid cervical trauma or uterine perforation. Also, contact of the sound with the vagina or with the blades of a speculum used to dilate the vagina should be avoided. Sounding therefore adds to the duration and complexity of the hydrotubation procedure and introduces an additional risk of cervical trauma and uterine perforation; even so, sounding cannot determine uterine depth with total accuracy.

Once the uterus has been sounded to determine its depth from cervix to fundus, a uterine cannula must be selected in which the length of the distal end portion between the cervical stop and the distal end does not exceed the measured depth of the uterus. If the distal end portion is too long, there is a distinct risk that the distal end of the cannula will perforate the uterus upon insertion of the cannula or upon manipulation of the uterus using the inserted cannula.

For reasons of safety, the cannulae that are most commonly available have distal end portions that are shorter than the depth of most uteri. Also, as sounding is an inexact procedure, it is necessary to err on the side of caution when interpreting the uterine depth measured by sounding. This means that in most cases, the cannula that is selected has a distal end portion that is too short to reach the fundus; indeed, the distal end of the cannula is often a considerable distance away from the fundus. This can reduce the effectiveness of fluid injection into the uterus and oviducts through the openings in the distal end portion. Also, where the distal end portion is not fully engaged within the uterus, the cannula may be less effective to manipulate the uterus.

Examples of uterine cannulae and manipulators include Spackman's Cannula; the ClearView uterine manipulator sold by Clinical Innovations; and the RUMI System sold by CooperSurgical, Inc. All trade marks are acknowledged. All of these examples have intra-uterine portions of a length that is predetermined to reduce the risk of uterine perforation.

The limitations of known uterine cannulae for manipulation mean that some physicians use cervical dilators as uterine manipulators. This, of course, increases the risk of uterine perforation. The risk of perforation can be reduced if a larger-diameter cervical dilator is used but this increases the difficulty of insertion into the cervix and the risk of cervical tearing and subsequent incompetence. Moreover a risk of perforation remains and if the uterus is perforated by a large-diameter dilator, the perforation will be worse and may give rise to heavy bleeding requiring proper repair of the uterine wall.

WO 2006/120451 discloses a uterine cannula in which the length of the distal end portion can be adjusted and set before use, following sounding of the uterus. The length of the distal end portion is adjusted to be just less than the length of the uterus as measured by a uterine sound. For safety in case of inaccurate sounding, the aim is to maintain a gap of at least 0.5 cm between the distal end of the instrument and the uterine fundus. Such a gap needs to be considered in the context of a typical uterine depth of just 6 to 8 cm.

The shaft of the uterine cannula of WO 2006/120451 comprises an inner tube and an outer tube. The inner tube is partially within the outer tube such that a distal end portion of the inner tube extends beyond the distal end of the outer tube. The inner tube is slideable coaxially within the outer tube, such that the length of the distal end portion is adjustable. The inner and outer tubes can then be locked together by a radial screw arrangement to fix the length of the distal end portion. A conduit extends along the inner tube and leads to apertures in the distal end portion for the injection of fluids such as dye.

The instrument of WO 2006/120451 suffers from the disadvantages that uterine sounding, with all its problems, is still necessary and that the cannula then has to be adjusted to suit the measured uterine depth and locked before use. Aside from the need to perform additional steps, there is a possibility that the cannula will be adjusted wrongly if sounding was inaccurate or if the measured uterine depth is misread or wrongly transcribed. Of particular concern is that if the distal end portion is mistakenly set too long for the uterus, the risk of perforation is considerably increased. Even where the uterine depth is measured and interpreted accurately, it is prudent to set the distal end portion too short for the uterus. This reduces the effectiveness of the cannula for uterine manipulation.

Whilst much of the distal end portion of the inner tube in WO 2006/120451 is curved, the outer tube is straight. The resulting overall shape of the instrument is like that of many uterine cannulae: predominantly straight with a minor curved portion at the distal end defined by the intra-uterine tip. When inserted into the patient's vagina in use, the proximal end of the cannula faces away from a physician using a laparoscope to inspect the pelvic region. This makes it difficult, if not impossible, for one physician to perform both laparoscopy and uterine manipulation. So, as before, two physicians may be needed to perform the procedure: one to use the laparoscope and the other simultaneously to manipulate the uterus with the cannula.

In a sealing arrangement similar to that of most uterine cannulae, the cannula of WO 2006/120451 further comprises a distally-tapering conical cervical stop positioned at or near to the distal end of the outer tube to seal within the external cervical os as aforesaid. The illustrated embodiments of WO 2006/120451 have a screw-threaded sealing surface. Screw-threaded cervical stops have been proposed for uterine cannulae for some years but have been found to cause trauma to the cervix and pain to the patient. Such measures are an attempt to overcome the fundamental difficulty of sealing to something as irregular and variable in size and shape as a cervix, but are not always successful. For example, the cervical os may range in diameter from stenosed to patulous, the latter potentially being substantially as wide as, if not wider than, the sealing surface of the cervical stop. In such a situation, effective sealing would be impossible with a normal conical cervical stop.

As an alternative to conical cervical stops in an effort to achieve a more reliable seal, some uterine cannulae include inflatable balloon-like sealing collars spaced along the shaft to lie both distally and proximally with respect to the cervix. However, such arrangements add considerably to the complexity and cost of the instrument. They also add to the diameter of the shaft, increasing the risk of cervical tearing and incompetence.

It is against this background that the present invention has been made.

From one aspect, the invention resides in a uterine manipulator comprising an elongate shaft having a distal end and a cervical stop positioned on the shaft proximally with respect to the distal end, wherein the distance between the stop and the distal end is variable in response to insertion of the manipulator into a patient's uterus in use.

By virtue of the invention, a universal uterine manipulator can adjust, or be adjusted, to suit all patients and all sizes of uterus. The manipulator allows far better exposure of the uterus than existing manipulators, even where the uterus is awkwardly oriented such as in an acutely retroverted position. Yet, the manipulator dramatically reduces, if not eliminates, the risk of uterine perforation.

Preferably, the length of the portion of the shaft between the distal end and the cervical stop is variable in response to insertion of the manipulator into a patient's uterus in use. For example, the shaft may comprise first and second shaft parts movable relative to each other, one of said shaft parts projecting distally beyond the other of said shaft parts. The shaft parts may be slideable relative to each other and may be offset laterally with respect to each other with respect to the longitudinal direction of the shaft. In preferred arrangements, the first shaft part is received by the second shaft part: for example, at least the second shaft part may be tubular and the shaft parts may be arranged for telescopic relative movement.

The first part suitably extends distally beyond the second part. Bias means may be provided for urging one of the shaft parts distally with respect to the other of the shaft parts, the bias means preferably acting between the shaft parts. The bias means may, for example, be a spring.

It is preferred that the first shaft part is hollow. In this way, for example, the first shaft part may define a fluid conduit that communicates with at least one hole penetrating a wall of the first shaft part. Such a fluid conduit may communicate with a proximal inlet. By means of the present invention, a fluid such as a dye may be injected into a patient's uterus by forcing the dye along the conduit. One or more holes in a distal portion of the instrument allow injected fluid to flow into the uterus.

The cervical stop may be fixed to the shaft or may be movable along the shaft. Where the cervical stop is movable along the shaft, the shaft suitably carries indicia such as a scale against which the position of the stop can be read for uterine sounding.

The stop may be moved by being slid along the shaft, and is preferably lockable to the shaft. For example, the stop may be locked in position by being clamped to the shaft. In that case, clamping may be effected by co-operable clamp parts that are movable relative to each other, a first clamp part acting on a second clamp part by virtue of said relative movement to cause the second clamp part to clamp against the shaft. Preferably at least one of the clamp parts is integral with the stop. The first clamp part is suitably disposed outwardly with respect to the second clamp part when the parts co-operate to clamp the second clamp part against the shaft. The clamp parts may surround the shaft, and at least the second clamp part is suitably a sliding fit with the shaft.

The clamp parts may be movable relative to each other in a longitudinal direction with respect to the shaft. That movement suitably effects clamping as aforesaid: for example, ramp formations of the clamp parts can co-operate upon relative longitudinal movement of the clamp parts to cause the second clamp part to clamp against the shaft. Preferably, the clamp parts comprise mutually co-operable threads.

To suit various diameters of cervical os, the cervical stop preferably has a sealing surface of variable diameter. For example, the stop may comprise cooperable relatively-movable stop parts that define respective sealing surface portions of successively greater diameter. A first, relatively narrow, stop part is suitably disposed distally with respect to a second, relatively wide stop part. The stop parts are preferably movable relative to each other in a longitudinal direction with respect to the shaft, for which purpose the stop parts are suitably a sliding fit with the shaft and may surround the shaft. The stop parts preferably comprise mutually co-operable inter-engagement formations such as mutually complementary threads.

The cervical stop preferably defines a sealing surface that tapers distally. For example, the sealing surface may be generally frusto-conical. The stop may also, or alternatively, comprise a plate or disc disposed transversely with respect to the shaft.

Advantageously, at least a portion of the shaft is curved along its length. Preferably at least a major portion of the shaft is curved along its length. It is also possible for the shaft to comprise successive portions that are inclined with respect to each other. More generally, a distal portion of the shaft may be co-linear with the remainder of the shaft, or the distal portion may be curved or angled relative to the remainder of the shaft.

At least a distal end portion of the shaft may be semi-rigid, and the shaft may be adapted for reversible use. For example, the shaft may have opposed ends of different diameters. Where the shaft has opposed ends, it suitably carries opposed cervical stops, one stop being associated with each end of the shaft. At least one of those opposed cervical stops is preferably movable along the shaft with respect to its associated end of the shaft.

The inventive concept encompasses a uterine manipulator comprising an elongate shaft having a distal end and a cervical stop positioned on the shaft proximally with respect to the distal end, wherein the stop is mounted for movement with respect to the shaft such that the distance between the stop and the distal end is variable by moving the stop.

The inventive concept may also be expressed in method terms. For example, the invention contemplates a method of inserting a uterine manipulator, comprising inserting a retractable distal end portion of the manipulator into a patient's uterus and causing the distal end portion to retract with respect to a proximal portion of the manipulator upon encountering the uterine fundus as the proximal portion advances distally until a cervical stop carried by the proximal portion bears against the patient's cervix.

An alternative expression of the inventive concept lies in a method of inserting a uterine manipulator, comprising inserting a distal end portion of the manipulator into a patient's uterus until a cervical stop carried by the manipulator bears against the patient's cervix; continuing insertion of the distal end portion into the uterus while the distal end portion advances distally with respect to the stop until the distal end of the manipulator encounters the uterine fundus; ceasing further insertion of the manipulator; and locking the stop with respect to the distal end portion. The stop may be locked while the distal end portion is within the uterus, or after the distal end portion has been withdrawn from the uterus. In that latter case, the distal end portion may be re-inserted into the uterus after the stop has been locked.

Any of the above methods of the invention may further comprise reading the distance between the distal end and the stop after withdrawal of the manipulator from the uterus.

Another method of inserting a uterine manipulator within the inventive concept comprises: measuring uterine depth; adjusting the position of a cervical stop carried by the manipulator with respect to a distal end of the manipulator in accordance with the measured uterine depth; and inserting a distal end portion of the manipulator into a patient's uterus until the stop bears against the patient's cervix.

Any of the above methods of the invention preferably further comprise performing hydrotubation and/or manipulation of the uterus after insertion of the manipulator. They may also comprise ascertaining the diameter of the cervical os and adjusting the width of the cervical stop to suit said diameter. This method may also be expressed broadly as a method of inserting a uterine manipulator, comprising ascertaining the diameter of the cervical os, adjusting the width of a cervical stop carried by the manipulator to suit said diameter, and inserting a distal end portion of the manipulator into a patient's uterus until the stop bears against the patient's cervix.

In some embodiments of the invention, spring-loaded axial adjustability of the length of the distal end portion of the instrument lowers the risk of perforation while increasing the manipulation capability of the cannula. Such embodiments of the invention also negate the requirement to measure uterine depth with a uterine sound prior to inserting a manipulator such as a cannula, thus reducing the length and complexity of the procedure.

The invention provides universal laparoscopic uterine manipulators such as cannulae and dilators with variable intra-uterine length to match the length of the uterus. This reduces the risk of perforation and provides excellent pelvic exposure irrespective of uterine size, shape and position. Moreover, semi-rigid (or semi-flexible) distal end portions described hereinafter are less likely to form false passages in the cervix and in the body of the uterus because they tend to follow the natural track of the cervical canal.

In order that the invention may be more readily understood, reference will now be made, by way of example, to the accompanying drawings in which.

Figure 1:
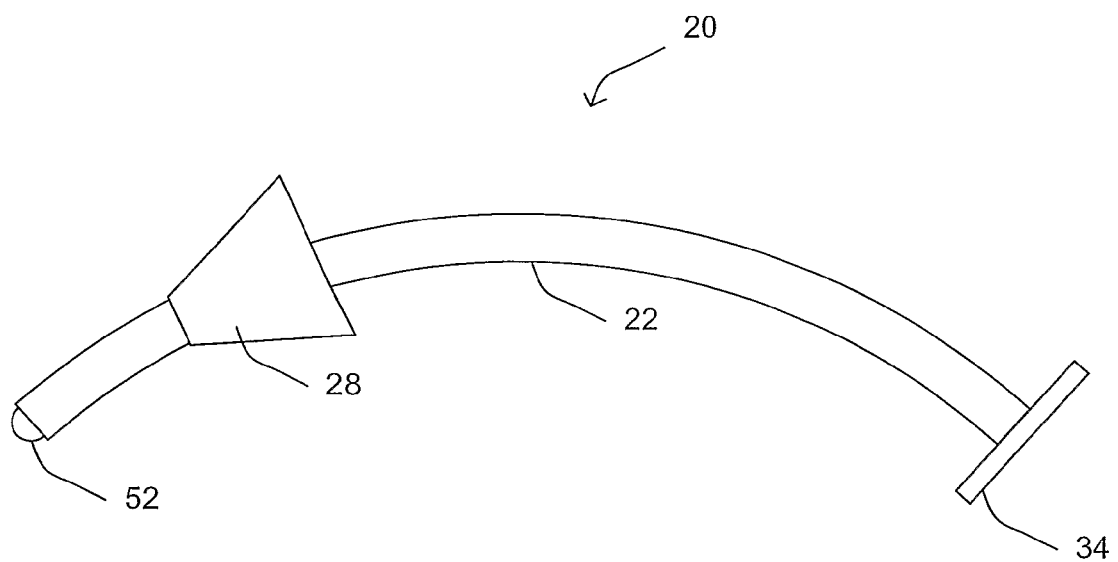
FIG. 1 is a schematic side view of a uterine cannula in a first embodiment of the present invention.
Figure 2:
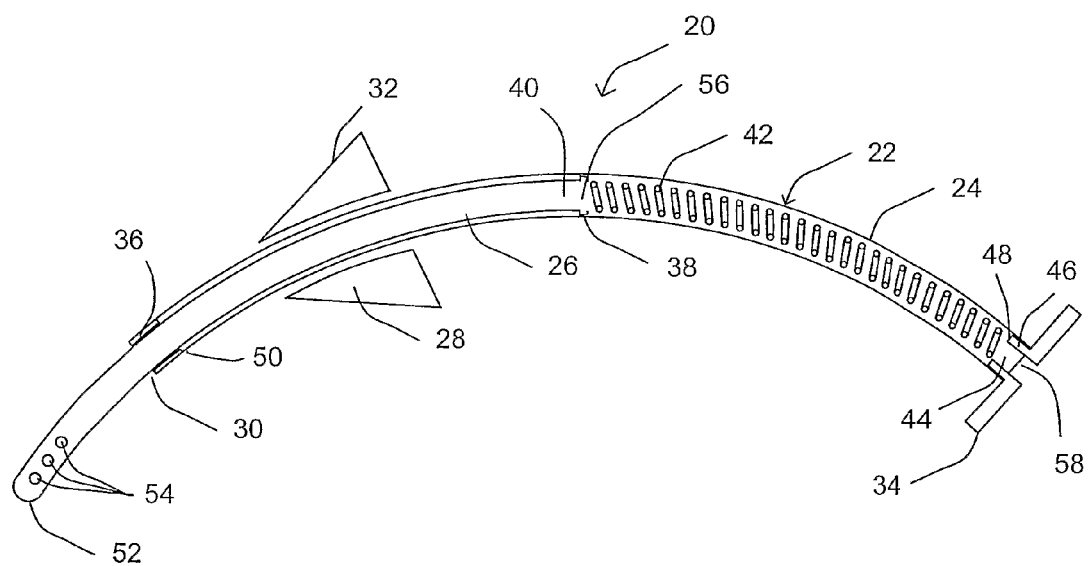
FIG. 2 is a schematic longitudinal section view corresponding to FIG. 1.
Figure 5:
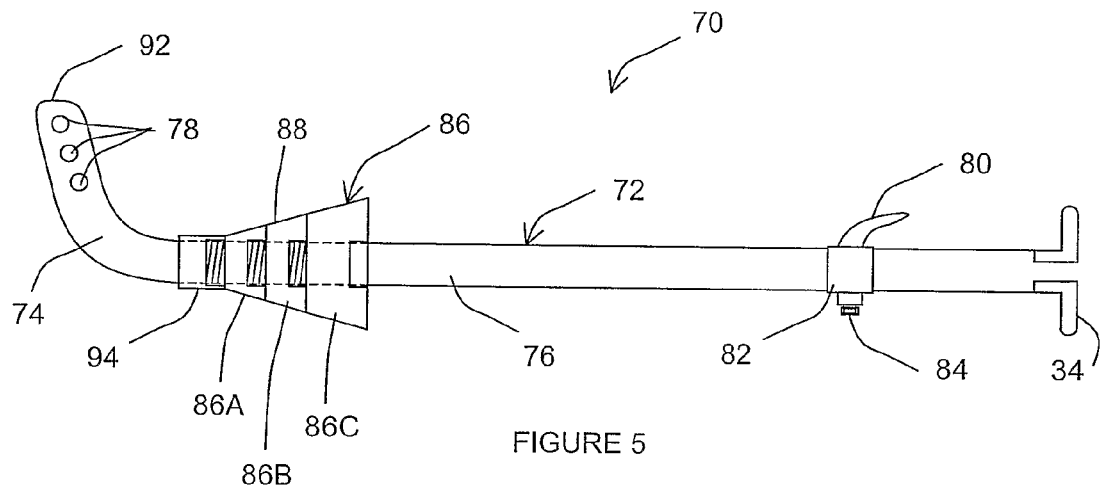
Figure 6:
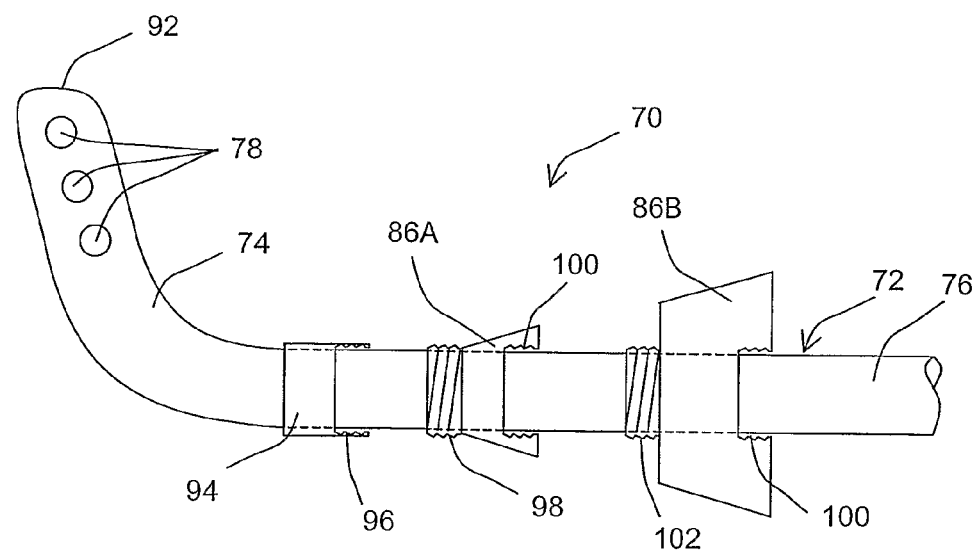
Figure 7A:
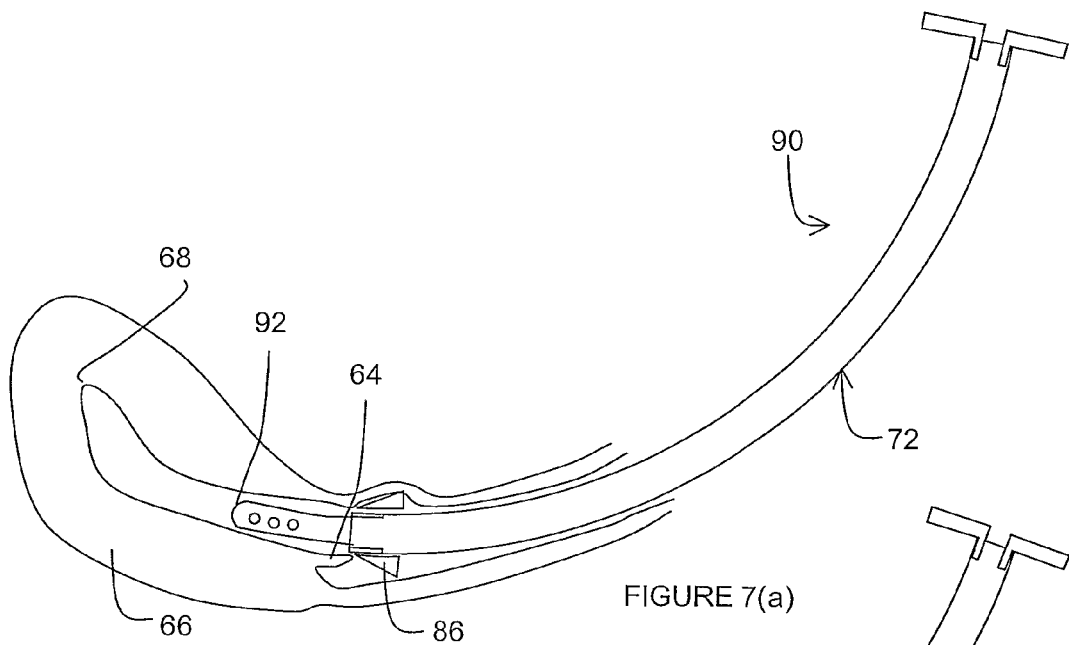
Figure 7B:
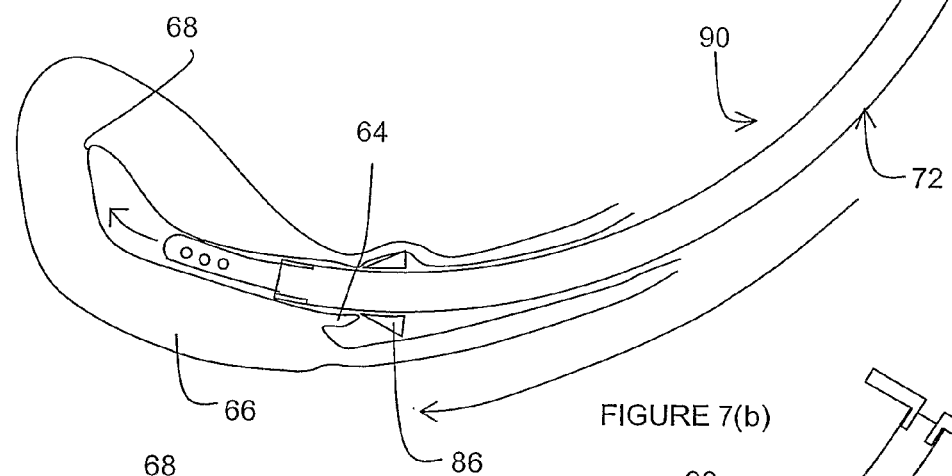
Figure 7C:
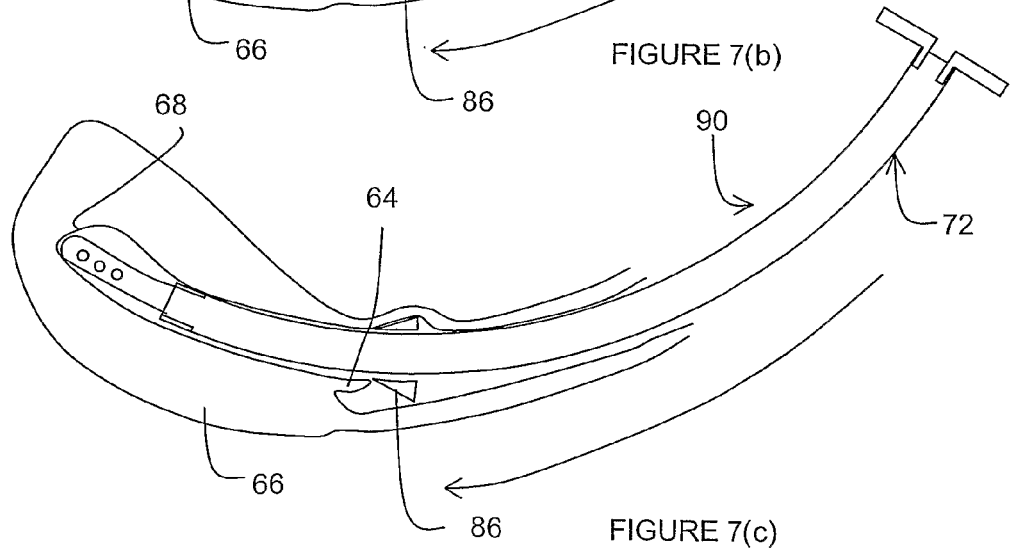
Figure 8:
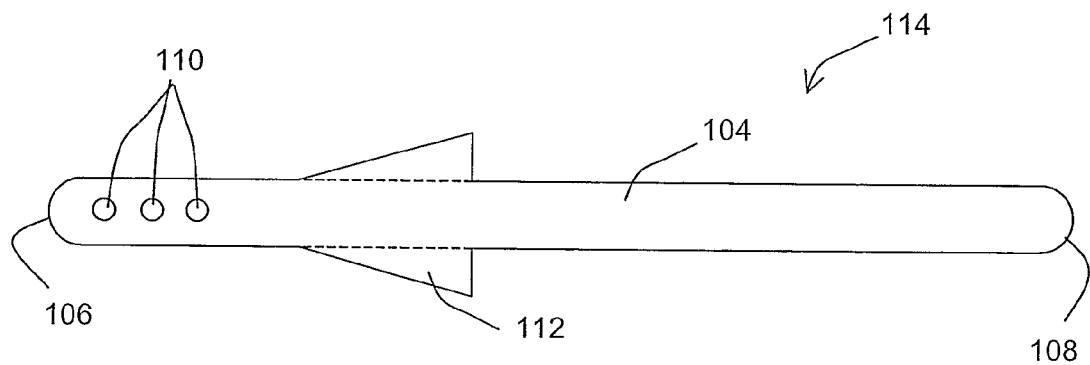
Figure 9:
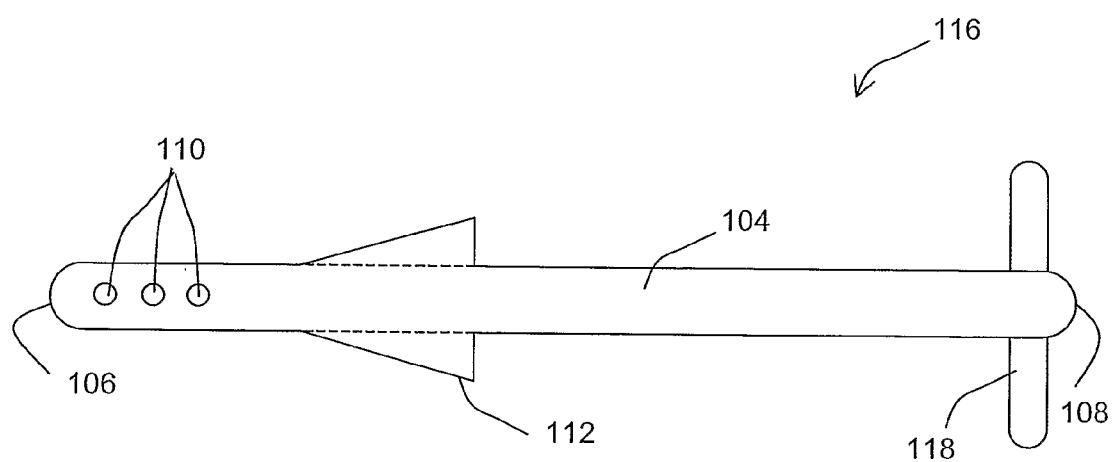
Figure 10:
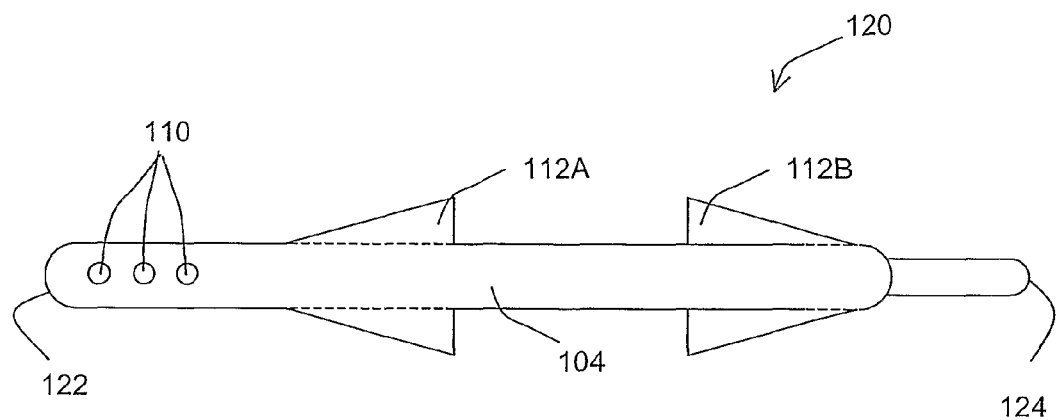
Figure 11:
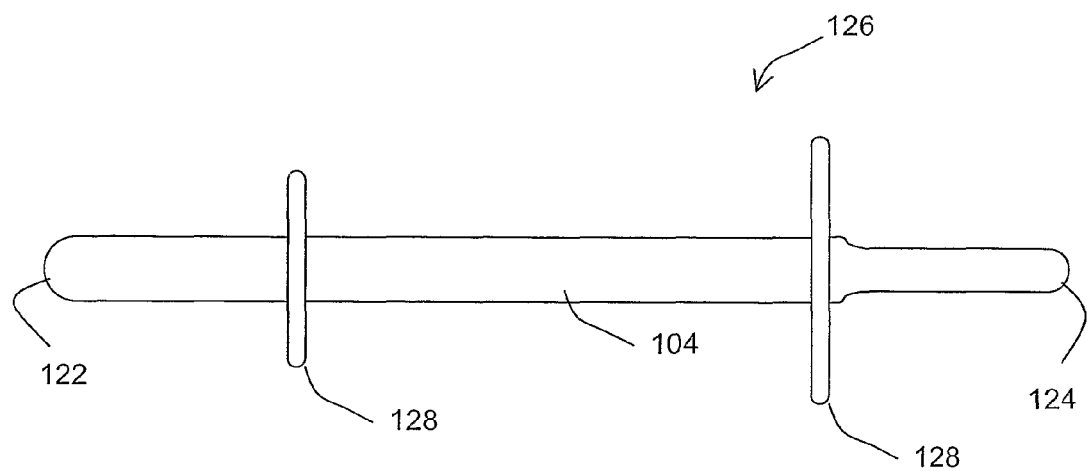

FIGS. 3(*a*) to 3(*c*) are a series of sectional side views of the cannula of FIGS. 1 and 2 in use on a patient;

FIGS. 4(*a*) and 4(*b*) are sectional side views showing how the cannula of FIGS. 1 and 2 can be used to reorient a retroverted uterus to an anteverted position;

FIG. 5 is a schematic side view of a uterine cannula with an adjustable cervical stop in a second embodiment of the invention;

FIG. 6 is an enlarged detail view showing a method of adjusting the cervical stop of the cannula of FIG. 5;

FIGS. 7(*a*) to 7(*c*) are a series of enlarged sectional side views showing a cannula in accordance with a third embodiment of the invention in use on a patient;

FIG. 8 is a schematic side view of a uterine dilator with a single cervical stop cone;

FIG. 9 is a schematic side view of a variant of the uterine dilator of FIG. 8;

FIG. 10 is a schematic side view of a reversible uterine dilator with opposed cervical stop cones; and FIG. 11 is a schematic side view of a reversible uterine dilator having discs serving as cervical stops.

Dimensions given in the following specific description are by way of illustration only, and do not limit the scope of the invention. Additionally, the illustrated embodiments are not drawn to scale.

According to a first embodiment of the invention shown in FIGS. 1 and 2, a cannula 20 comprises a hollow shaft 22 about 30 cm long that is curved along its length and is of circular cross-section. As best shown in FIG. 2, the shaft 22 comprises an outer tube 24 and an inner tube 26 slideable telescopically within the outer tube 24 to protrude to a varying extent from the open distal end of the outer tube 24.

By way of example, the outer tube 24 may be about 7 mm in external diameter and about 6 mm in internal diameter. The inner tube 26 may be about 5 mm in external diameter. It will therefore be apparent that there is clearance between the tubes 24, 26 along much of their shared length.

A cervical stop 28 is fixed to the outer tube 24 near its distal end 30, in this example about 6 cm from the distal end 30. The cervical stop 28 has a frusto-conical sealing surface 32 that tapers distally toward the outer tube 24. The outer tube 24 also has an integral or detachable handle 34 at its proximal end.

With specific reference to FIG. 2, it will be noted that the outer and inner tubes 24 and 26 are of concentric cross-section and have matching curvature. A tubular insert 36 fixed inside the distal end 30 of the outer tube 24 defines an annular bearing surface for sliding movement of the inner tube 26 within. The insert 36 is about 1 cm long in this instance and has a wall thickness of about 0.5 mm to define an internal diameter of about 5 mm for a sliding fit with the external diameter of the inner tube 26. The inner tube 26 has a disc 38 of about 6 mm diameter at its proximal end 40 that defines an annular bearing flange for sliding contact with the inner surface of the outer tube 24.

The bearing surface defined by the insert 36 and the bearing flange defined by the disc 38 support the inner tube 26 for sliding movement within and with respect to the outer tube 24. Moreover the bearing flange defined by the disc 38 seals against the inner surface of the outer tube 24 to retain fluids such as dye within the hollow shaft 22.

A compression spring 42 acts between the proximal end 40 of the inner tube 26 and the proximal end 44 of the outer tube 24. It will be noted in this respect that the handle 34 is of T-section, having a tubular stem 46 that fits within the open proximal end of the outer tube 24. The internal diameter of the tubular stem is about 5 mm. The stem 46 defines a shoulder 48 against which the proximal end of the spring 42 bears. The distal end of the spring 42 bears against the disc 38 at the proximal end of the inner tube 26.

The insert 36 at the distal end 30 of the outer tube 24 defines a proximal shoulder 50 against which the disc 38 at the proximal end of the inner tube 26 bears when the spring 42 and hence the inner tube 26 is fully extended. This prevents the inner tube 26 falling out of the outer tube 24 when fully extended, as the spring 42 remains under compression.

The inner tube 26 has a blunt, blind distal end 52. A series of a holes 54 penetrate the wall of the inner tube 26 proximally of the distal end 52 to allow fluid to flow from or into the interior of the inner tube 26. That fluid is admitted to or received from the inner tube 26 through an opening 56 defined by a central hole that penetrates the disc 38 at the proximal end of the inner tube 26. The interior of the outer tube 24 communicates with the interior of the inner tube 26 through the opening 56 and communicates, in turn, with a further opening 58 at the proximal end of the outer tube 24. The opening 58 may be adapted for coupling with the distal end of a syringe (not shown) for the introduction of fluid such as a dye.

Figure 3A:
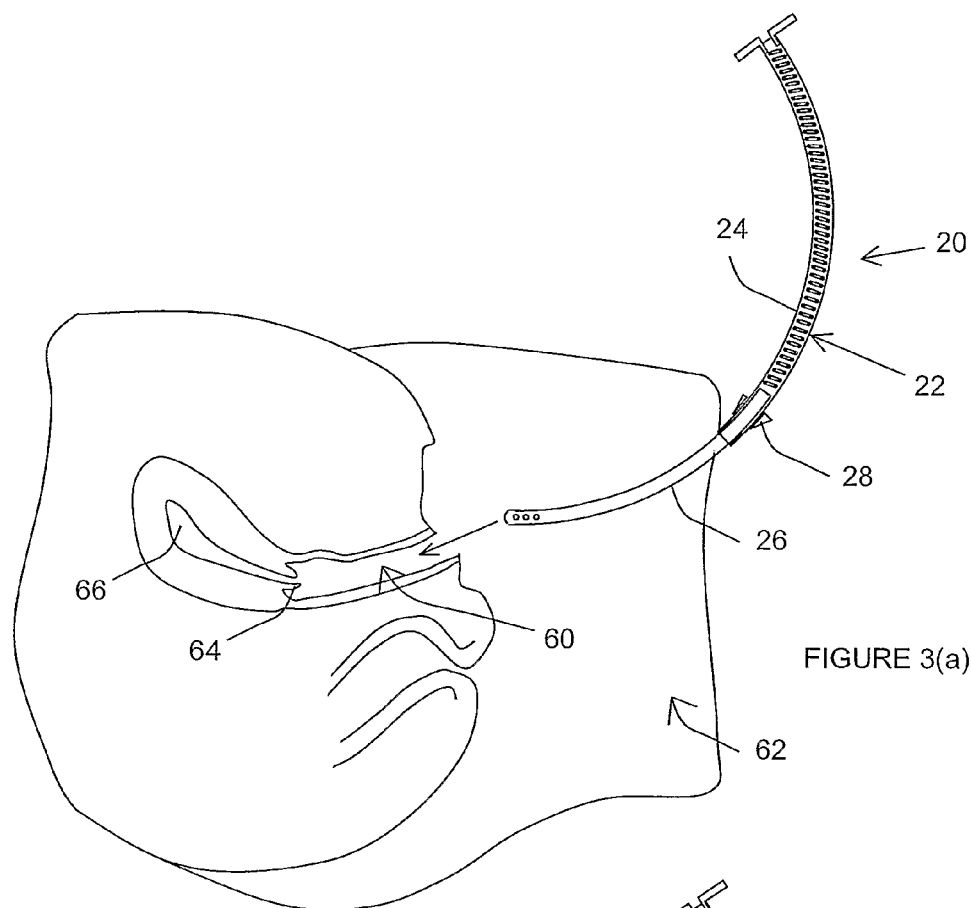
Figure 3B:
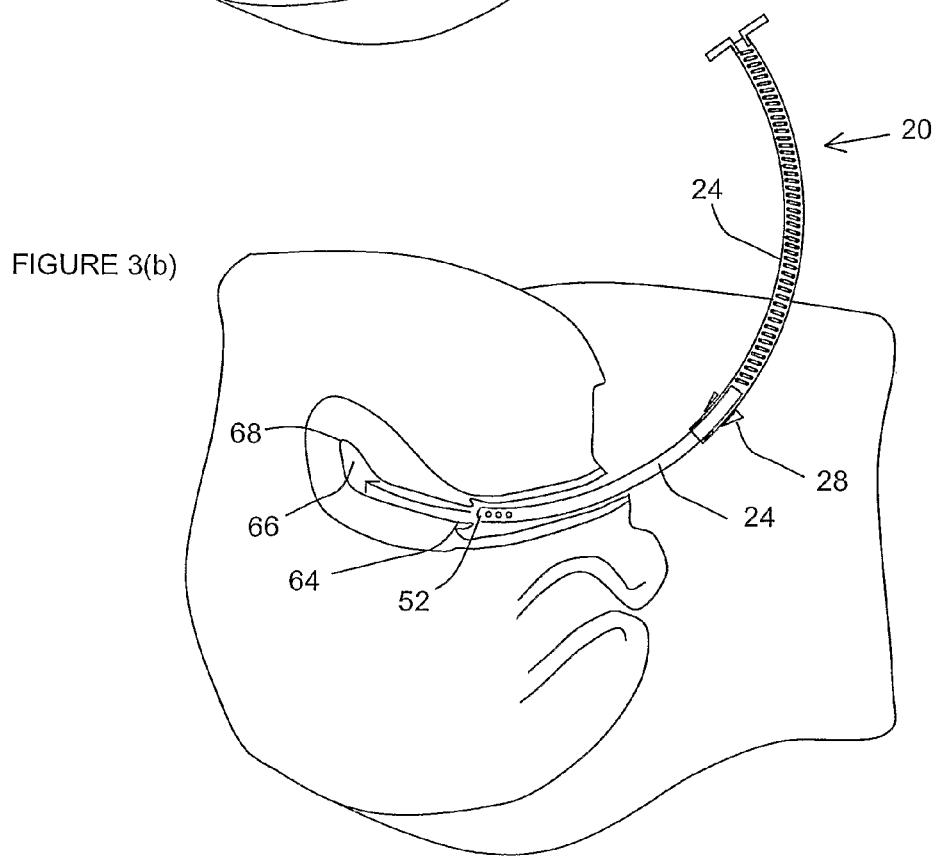
Figure 3C:
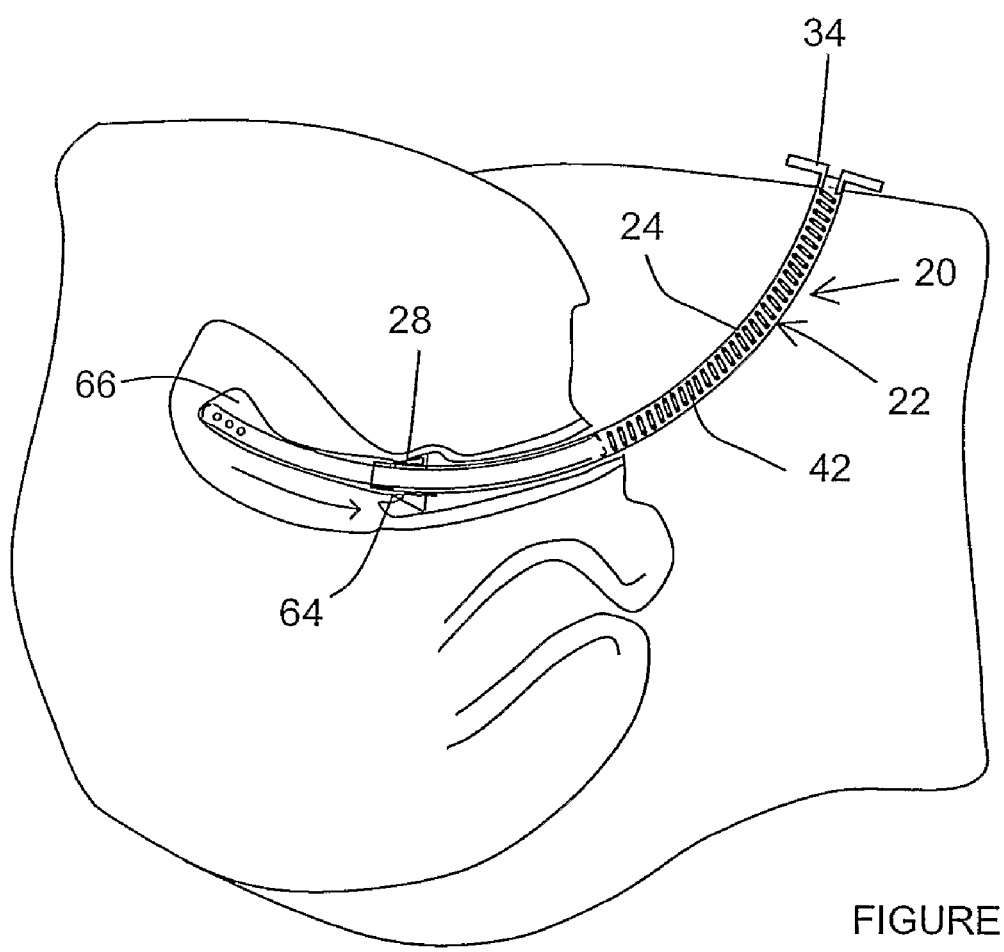

Referring now to FIGS. 3(a) to 3(c) of the drawings, these Figures show the embodiment of FIGS. 1 and 2 in use. FIG. 3(a) shows the cannula 20 in its relaxed state with the inner tube 26 fully extended from the outer tube 24 and ready for insertion into the vagina 60 of a patient 62. As shown in FIG. 3(b), the narrow inner tube 26 can fit easily into the os of the cervix 64 and from there into the uterus 66 as shown in FIG. 3(c). FIG. 3(c) also shows that the distal end portion of the outer tube 24 enters the cervical os until the sealing surface 32 of the cervical stop 28 engages with the external os of the cervix 64 and seals to it.

As the cannula 20 moves distally from the partially-inserted state in FIG. 3(b) to the fully-inserted state in FIG. 3(c), the distal end 52 of the inner tube 26 bears against the fundus 68 of the uterus 66. This causes the inner tube 26 to retract into the outer tube 24 against the bias of the spring 42. Thus, the intrauterine length of the cannula 20 between the distal end 52 of the inner tube 26 and the sealing surface 32 of the cervical stop 28 varies in response to insertion of the cannula 20 into the uterus 66, effecting automatic adjustment of the intra-uterine length to suit the dimensions of the uterus 66.

With the intra-uterine length of the cannula 20 closely matching the length of the uterus 66 from cervix 64 to fundus 68, the cannula 20 can be manipulated to effect reliable and easily-controllable movement of the uterus 66 during laparoscopic procedures. Yet, there is minimal risk of damage to the uterus 66 such as perforation. There is no longer a need for an assistant to manipulate the cannula 20 during a laparoscopic procedure as the curvature of the shaft 22 presents the handle 34 upwardly in a convenient location where it can be grasped easily by the physician performing laparoscopy.

Dye or other fluids can readily be introduced or aspirated as part of the procedure. For this purpose, the distal parts of both the outer tube 24 and the inner tube 26 could have holes in their walls to allow injection and aspiration of fluids if required. The substantially fluid-tight seal formed between the cervix 64 and the stop 28 means that injected fluid such as dye remains substantially within the uterus 66 until the seal is broken at the end of the procedure.

As will be described below in relation to a second embodiment of the invention shown in FIGS. 5 and 6, forceps attachment means may be provided on the shaft 22 of the cannula 20. Using the attachment means, a tenaculum or volsellum forceps may be attached to the cannula 20 and to the cervix 64 to stabilise the uterus 66 and to keep the sealing surface 32 of the cervical stop 28 in sealing contact with the cervix 64 during subsequent procedures. However, such forceps have been omitted from the drawings for clarity.

Figure 4A:
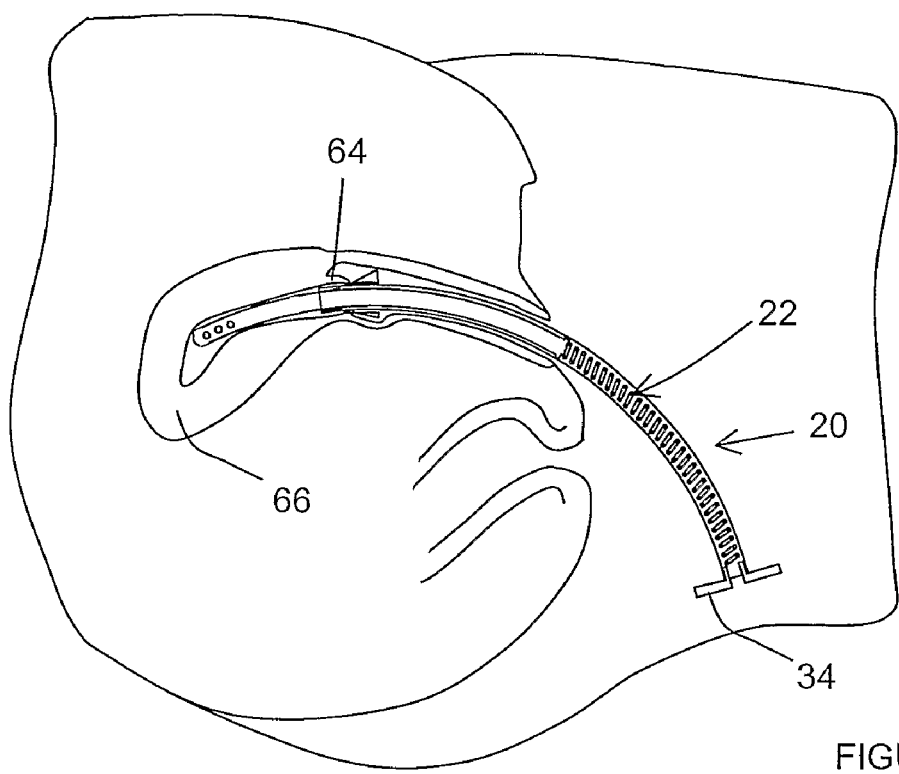
Figure 4B:
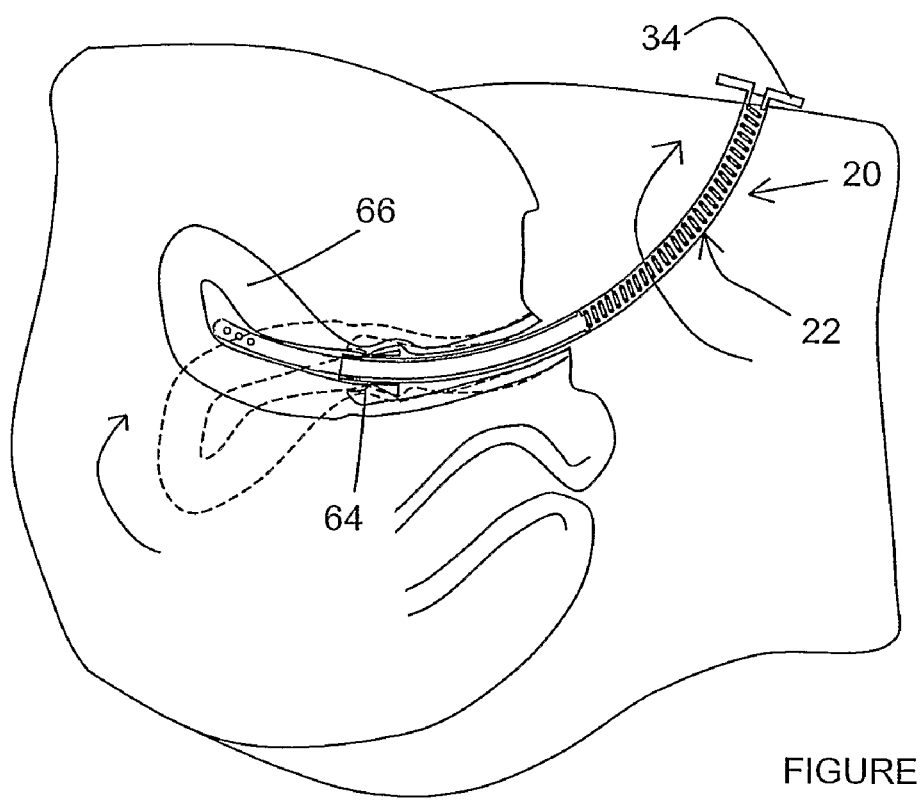

FIGS. 4(a) and 4(b) show that the curvature of the shaft 22 of the first embodiment has a further advantage when a retroverted uterus is encountered as shown in FIG. 4(a). Here, the cannula 20 can be oriented with the handle 34 facing downwardly so that the distal end portion of the cannula 20 also faces downwardly. This eases insertion of the distal end portion into the retroverted uterus 66. When the distal end portion is fully engaged within the uterus 66 and the cervical stop 28 is engaged with the cervix 64, the cervix 64 can be used as a fulcrum about which the cannula 20 is turned through 180° until the handle 34 faces upwardly. The distal end portion of the cannula 20 thereby turns within the uterus 66 and lifts about the fulcrum of the cervix 64 to reorient the uterus 66 into the anteverted position shown in FIG. 4(b). In the anteverted position, exposure of the uterus 66 and the associated oviducts and ovaries (not shown) is improved.

In a second embodiment of the invention shown in FIGS. 5 and 6, a uterine cannula 70 has a hollow shaft 72 that comprises a curved minor distal portion 74 fixed to a straight major proximal portion 76. Again, openings 78 in the distal portion 74 permit injection and aspiration of fluids such as dye. The curvature of the distal portion 74 is slightly exaggerated in these drawings.

FIG. 5 shows a forceps attachment means in the form of a proximally-directed hook 80 for attachment of forceps to the cannula 70: forceps attachment means like this can be applied to any embodiment of the invention. The hook 80 projects radially from a collar 82 that can be slid along the proximal portion 76 of the shaft 72 and locked in a desired position by the clamping action of a screw 84.

As in the first embodiment, a cervical stop 86 mounted on the shaft 72 defines a frusto-conical sealing surface 88 that tapers distally. In the second embodiment, the stop 86 is shown divided into three portions 86A, 86B and 86C in distal-to-proximal order. The purpose of dividing the stop 86 in this way will be explained later.

The key difference between the first and second embodiments is that in the second embodiment, the stop 86 is movable proximally and distally relative to the underlying shaft 72. That movement is preferably by longitudinal sliding along the shaft 72.

A movable cervical stop 86 can be applied to any embodiment of the invention but has particular importance in embodiments like that of FIGS. 5 and 6 where the shaft 72 is of fixed length. Similarly, FIGS. 7(*a*) to 7(*c*) show a third embodiment of the invention in the form of a cannula 90 in which substantially all of the length of the shaft 72 is curved like the first embodiment but is of fixed length like the second embodiment. Otherwise, like numerals are used for like parts in FIGS. 5, 6 and 7(*a*) to 7(*c*). In these embodiments, the stop 86 must move to vary the distance between the stop 86 and the distal end 92, hence to change the length of the intra-uterine distal end portion of the cannula 70, 90. The distal end 92 is blunt and blind as in the first embodiment.

Movement of the cervical stop 86 along the shaft 72 can be effected either before insertion of the cannula 70, 90 into the uterus 66 or, preferably, during insertion.

In the first case, where movement of the cervical stop 86 along the shaft 72 is effected before insertion of the cannula 70, 90 into the uterus, the uterus is first sounded, for example with the cannula 70, 90, to determine its depth and the stop 86 is slid along the shaft 72 to match the length of the distal end portion to the measured uterine depth. The position of the stop 86 with respect to the shaft 72 may be read on a scale (not shown) marked along the shaft 72. The stop 86 is then locked to the shaft 72 in the appropriate position and the distal end portion of the shaft 72 is inserted through the cervix 64 into the uterus 66 until the stop 86 engages with the external os of the cervix 64 to limit further insertion of the distal end portion.

In the second case, where movement of the cervical stop 86 along the shaft 72 is effected during insertion of the cannula 70, 90 into the uterus 66, the stop 86 is not initially locked to the shaft 72 of the cannula 70, 90 before first insertion into the uterus 66. Upon first insertion, the distal end portion of the cannula 70, 90 enters the cervix 64 and continues moving distally into the uterus 66 with continued insertion. This is shown, in relation to the third embodiment, in FIG. 7(*a*). Eventually the stop 86 encounters the cervix 64 and engages with the external cervical os, which blocks further distal movement of the stop 86 as shown in FIG. 7(*b*); however, the shaft 72 is still free to move distally by sliding within the stop 86. The length of the intra-uterine portion therefore increases from when the stop 86 engages with the cervix 64 until the distal end 92 of the shaft 72 encounters the uterine fundus 68 as shown in FIG. 7(*c*). As when sounding, the physician feels for increasing resistance as the distal end 92 encounters the fundus 68.

During insertion of the cannula 70, 90 in this manner, the stop 86, in effect, slides proximally with respect to the shaft 72. The stop 86 may then be locked to the shaft 72 in a proximally-displaced position that defines a distal end portion length corresponding to the uterine depth. The cannula 70, 90 may be withdrawn and re-inserted into the uterus 66 after the stop 86 has been locked in that position. For example, the cannula 70, 90 may be withdrawn from the vagina without further displacing the stop 86, whereupon the stop 86 is locked to the shaft 72 and the position of the stop 86 with respect to the shaft 72 may be read on a scale (not shown) marked on the shaft 72 to interpret the uterine depth. Alternatively, to avoid the need for re-insertion, the stop 86 can be locked in a proximally-displaced position when the cannula 70, 90 is in situ within the uterus 66.

In this second case, the degree of friction between the stop 86 and the shaft 72 that resists movement of the stop 86 along the shaft 72 should be determined carefully. The friction that has to be overcome to move the stop 86 along the shaft 72 should not be too high; otherwise, a dangerously high force would have to be applied to the shaft 72 to move it distally into the uterus 66 once the stop 86 has engaged with the cervix 64. But nor should the friction be too low, because that friction holds the stop 86 in the desired position when the desired intra-uterine length has been achieved but before the stop 86 is locked to the shaft 72.

In either of the above cases, when the stop 86 is locked to the shaft 72 and engaged with the cervix 64, the cannula 70, 90 can be used for hydrotubation and uterine manipulation. The physician can perform these actions safe in the knowledge that the intra-uterine portion extends the full length of the uterus 66 for ease of manipulation, but not so far as to increase the risk of uterine perforation.

FIGS. 5 and 6 show how the cervical stop 86 can be locked to the shaft 72 by a clamping means, in the context of the second embodiment. Similar clamping means can be applied to the third embodiment of FIGS. 7(*a*) to 7(*c*) or indeed to any embodiment in which a cervical stop is movable relative to an underlying shaft.

In FIGS. 5 and 6, the clamping means comprises mutually-cooperable clamp parts. A first clamp part in the form of an annular collar 94 encircles the shaft 72 and has a distal end that is a sliding fit around the shaft 72. The collar 94 has a female thread 96 leading distally from the proximal end of the collar 94. A second clamp part in the form of the distal cervical stop portion 86A, that is also a sliding fit around the shaft 72, has a male thread 98 at its annular distal end that is complementary to the female thread 96 of the collar 94.

When their threads 96, 98 are partially engaged, the collar 94 and the stop portion 86A are united for sliding movement together along the shaft 72. Alternatively, the stop portion 86A can be disengaged completely from the collar 94 and slid separately along the shaft 72. When the threads 96, 98 are more fully engaged, the female thread 96 of the collar 94 advances along the male thread 98 of the stop portion 86A. This causes the collar 94 to apply an inward force to the distal end of the stop portion 86A which in turn applies an inward clamping force to the shaft 72, increasing friction between the stop portion 86A and the shaft 72. Thus the friction acting between the stop portion 86A and the shaft 72 that resists movement of the stop portion 86A along the shaft 72 can be adjusted by turning the collar 94 about the stop portion 86A to vary the extent of engagement between the threads 96, 98 When the female thread of the collar 94 is advanced fully along the male thread of the stop portion 86A, the clamping force applied to the shaft 72 increases to the extent that the stop portion 86A is eventually locked to the shaft 72.

The engaging threads 96, 98 may be shaped or dimensioned to clamp the stop portion 86A in the manner described. For example, the female thread 96 may be slightly undersize for the male thread 98, or the male thread 98 may have a shallow ramp profile that rises proximally away from the shaft 72 so that the collar 94 applies increasing inward force as the female thread 96 progresses proximally along the male thread 98

As mentioned previously and as shown in FIG. 5, the cervical stop 86 is in three portions 86A, 86B and 86C. Only two of those stop portions (86A and 86B) are shown in FIG. 6, the largest stop portion 86C having been detached from the other stop portions and slid proximally along the shaft 72 in that instance.

The stop portions 86A, 86B and 86C define respective frusto-conical sealing surface portions of successively greater diameter in the proximal direction. The sealing surface portions cooperate to define the smooth frusto-conical sealing surface 88 of the stop 86 as a whole. Thus, the middle stop portion 86B is flanked distally by the relatively narrow stop portion 86A and is flanked proximally by the relatively wide stop portion 86C. All of the stop portions 86A, 86B and 86C are slideable longitudinally relative to each other and with respect to the shaft.

As best shown in FIG. 6, the stop portions 86A, 86B and 86C comprise mutually co-operable inter-engagement formations in the form of mutually complementary threads. Specifically, the stop portions 86A and 86B each have a female thread 100 leading distally from their respective proximal ends. The stop portions 86B and 86C each have a male thread 102 at their respective distal ends that are complementary to the female threads 100. Thus, each of the stop portions 86B and 86C can be slid distally along the shaft 72 and turned about the shaft to bring its male thread 102 into engagement with the female thread 100 of the succeeding stop portion 86A or 86B. Once engaged to each other in this way and fully tightened, the stop portions 86A, 86B and 86C cooperate to define a sealing surface whose size depends on how many of the stop portions 86A, 86B and 86C are selected for use. Thus, in preferred aspects of the present invention, the diameter of the sealing surface 88 of the cervical stop 86 can thereby be varied to suit various diameters of the cervical os. The stop 86 and the stop portions 86A, 86B and 86C could be of any suitable dimensions.

Whilst the invention has been described in the context of a uterine cannula having provision to inject or to aspirate fluid through a hollow interior, this is not essential. For example, in a broad sense, the invention encompasses arrangements in which the distal end portion, or indeed the shaft as a whole, is solid.

Preferably the cervical stop is made from a plastics material but it could also be made from stainless steel or any other suitable material.

Moving finally to FIGS. 8 to 11, these drawings show how aspects of the above embodiments of the invention can be used in uterine dilators to reduce the risk of uterine perforation. Once inserted into the uterus, such dilators may also be used as uterine manipulators. For this reason, the term 'uterine manipulator' in this specification encompasses uterine dilators, whether or not they are in fact used for manipulation.

In each of FIGS. 8 to 11, the dilator has a shaft 104 comprising a graduated curved or straight tube or bar of fixed length or with a retractable distal end portion of any suitable diameter. The shaft 104 has a blind distal end 106 and either a blind or open proximal end 108. If the shaft 104 is tubular, preferably a multiplicity of holes 110 perforates the side wall of the distal part of the shaft 104. A cervical stop 112 could be fixed near the distal end 106 of the shaft 104 (for example about 6 cm away) or could, preferably, be slideably adjustable along the shaft as explained above in relation to the second and third embodiments. Similarly, the stop 112 could be divided like the stop 86 of the second embodiment to suit different diameters of cervical os, the parts of the stop fitting together to form a larger whole.

The dilators shown in FIGS. 8 to 11 are intended to be used after the uterus has been sounded to determine its depth. The cervical stop 112 can then be positioned on the shaft 104 to suit the measured uterine depth, and fixed in that position. The dilator is then used to dilate the cervix to the desired diameter, preferably greater than 5 mm, whereupon the dilator can be used safely as a manipulator.

Preferably at least a distal end portion of the shaft 104 of the dilators shown in FIGS. 8 to 11 is semi-rigid to ease probing and dilation of the cervix while reducing the possibility of uterine perforation. A semi-rigid distal end portion of the dilator will tend to follow the natural path of the cervical canal by virtue of its flexible nature. This helps to avoid forming a false passage through the cervix, which is a significant cause of uterine perforation. A semi-rigid distal end portion could be applied to any of the first to third embodiments of the invention.

The uterine dilator 114 in FIG. 8 has a straight shaft 104 carrying a conical stop 112. The uterine dilator 116 in FIG. 9 is like that shown in FIG. 8 but adds a handle 118 at the proximal end 108.

FIG. 10 shows a uterine dilator 120 having a straight shaft 104 whose opposed ends 122 and 124 are of different diameters. Thus, the dilator 120 may be reversed to suit different diameters of cervical os, or to start dilation with the narrower end 124 and then to continue dilation with the wider end 122. In this case, opposed cervical stops 112A and 112B are used, one for each end 122, 124 of the dilator 120. Again, the longitudinal position of at least one of the stops 112A and 112B may be adjustable using the principle explained above in relation to the second embodiment.

FIG. 11 shows a dilator 126 that again has a straight shaft 104 whose opposed ends 122 and 124 are of different diameters for reversible use. As an alternative to the conical stops 112 of the preceding embodiments, the dilator 126 has disc-shaped cervical stops 128 disposed in parallel planes that are orthogonal to the central longitudinal axis of the shaft 104.

In its various embodiments, the invention provides an instrument for uterine manipulation and other gynaecological procedures that can adapt, or be adapted, to suit all types, shapes and sizes of uteri and cervixes. The instruments of the invention drastically reduce the risk of uterine perforation or cervical trauma, while offering far better exposure than other uterine manipulators.

The invention claimed is:

1. A uterine manipulator comprising an elongate shaft having a distal end, a proximal end, a cervical stop positioned on the shaft proximally with respect to the distal end, and a bias means for biasing the distal end with respect to the proximal end so that the distance between the stop and the distal end adjusts automatically to suit the length of a patient's uterus on insertion of the manipulator into the uterus.

2. The manipulator of claim 1, wherein the shaft comprises first and second shaft parts movable relative to each other, one of said shaft parts projecting distally beyond the other of said shaft parts.

3. The manipulator of claim 2, wherein the shaft parts are slideable relative to each other.

4. The manipulator of claim 2, wherein the shaft parts are offset laterally with respect to each other with respect to the longitudinal direction of the shaft.

5. The manipulator of claim 2, wherein the first shaft part is received by the second shaft part.

6. The manipulator of claim 5, wherein the second shaft part is tubular.

7. The manipulator of claim 5, wherein the shaft parts are arranged for telescopic relative movement.

8. The manipulator of claim 5, wherein the first part extends distally beyond the second part.

9. The manipulator of claim 2, wherein the bias means is arranged for urging one of the shaft parts distally with respect to the other of the shaft parts.

10. The manipulator of claim 9, wherein the bias means acts between the shaft parts.

11. The manipulator of claim 9, wherein the bias means is a spring.

12. The manipulator of claim 2, wherein the first shaft part is hollow.

13. The manipulator of claim 12, wherein the first shaft part defines a fluid conduit that communicates with at least one hole penetrating a wall of the first shaft part.

14. The manipulator of claim 13, wherein the fluid conduit communicates with a proximal inlet.

15. The manipulator of claim 1, wherein the cervical stop is fixed to the shaft.

16. The manipulator of claim 1, wherein the stop defines a generally frusto-conical sealing surface that tapers distally.

17. The manipulator of claim 1, wherein the stop comprises a plate disposed transversely with respect to the shaft.

18. The manipulator of claim 1, wherein at least a portion of the shaft is curved along its length.

19. The manipulator of claim 1, wherein at least a major portion of the shaft is curved along its length.

20. The manipulator of claim 1, wherein the shaft comprises successive portions that are inclined with respect to each other.

21. The manipulator of claim 1, wherein at least a distal end portion of the shaft is semi-rigid.

22. The manipulator of claim 1, wherein the shaft is adapted for reversible use.

23. The manipulator of claim 22, wherein the shaft has opposed ends of different diameters.

24. The manipulator of claim 22, wherein the shaft has opposed ends and carries opposed cervical stops, one being associated with each end.

25. The manipulator of claim 24, wherein at least one of the opposed cervical stops is movable along the shaft with respect to its associated end.

26. The manipulator of claim 1, wherein the cervical stop has a sealing surface of variable diameter.

27. A uterine manipulator comprising an elongate shaft adapted for reversible use, wherein the shaft has opposed ends and carries opposed cervical stops, one being associated with each end, said stops being mounted for movement with respect to the shaft such that the distance between each stop and its associated end is variable by moving said each stop.

28. The manipulator of claim 27, wherein at least one of the opposed cervical stops is movable along the shaft with respect to its associated end.

* * * * *